(12) United States Patent
Grassano

(10) Patent No.: US 11,833,323 B2
(45) Date of Patent: Dec. 5, 2023

(54) HAND-HELD POWER TOOL HAVING GRASP-ACTIVATED POWER SWITCH

(71) Applicant: Mark Vincent Grassano, Downington, PA (US)

(72) Inventor: Mark Vincent Grassano, Downington, PA (US)

( * ) Notice: Subject to any disclaimer, the term of this patent is extended or adjusted under 35 U.S.C. 154(b) by 0 days.

(21) Appl. No.: 18/118,073

(22) Filed: Mar. 6, 2023

(65) Prior Publication Data

US 2023/0201552 A1 Jun. 29, 2023

Related U.S. Application Data

(63) Continuation-in-part of application No. 17/235,847, filed on Apr. 20, 2021.

(60) Provisional application No. 63/316,951, filed on Mar. 4, 2022, provisional application No. 63/012,772, filed on Apr. 20, 2020.

(51) Int. Cl.
*A61M 37/00* (2006.01)
*H02J 7/00* (2006.01)
*H02K 7/14* (2006.01)

(52) U.S. Cl.
CPC ....... *A61M 37/0076* (2013.01); *H02J 7/0042* (2013.01); *H02K 7/145* (2013.01); *A61M 2205/8206* (2013.01)

(58) Field of Classification Search
CPC .............. A61M 37/00; A61M 37/0076; A61M 37/0084; A61M 2205/3592; A61M 2205/8206; A61B 90/39; A61B 2090/395; A61B 2090/3937; A01K 11/00; A61N 5/0616; A61N 5/0642; A61N 5/0647; A61N 5/0652; H02J 7/0042; H02J 7/0063; H02J 50/20; H02K 7/145; H05K 5/0247; B25F 5/00; B25F 5/02; B23K 3/30346;
(Continued)

(56) References Cited

U.S. PATENT DOCUMENTS 196,747 A 11/1877 Edison
464,801 A 12/1891 OReilly
(Continued)

OTHER PUBLICATIONS

International Preliminary Report on Patentability dated Nov. 3, 2022 for PCT/US2021/028257.
(Continued)

*Primary Examiner* — Robert J Scruggs
(74) *Attorney, Agent, or Firm* — Burdick Patents, P.A.; Sean D. Burdick; Colin L. Honan

(57) ABSTRACT

A grasp-activated power switch is integrated within a handle for a hand-held power tool. The switch has an outer shell defining an inner channel with a first and second pin extending therein. The tool body has a first and second conductor. A motor within the tool body is electrically connected to one of the first or second conductors and to an internal battery. The internal battery is connected to the other of the first or second conductors. On its surface the outer shell has actuating and non-actuating areas. A manual grasping force when applied to the actuating area connects the first and second pins with the first and second conductors to complete an electrical circuit. The closure energizes the tool motor. With each grasp, the switch toggles power to the motor off or on, and when on, the motor transmits power through the inner channel.

19 Claims, 14 Drawing Sheets

(58) Field of Classification Search
CPC ..... B26B 21/40; B26B 21/4056; B23D 51/01; B23D 51/10
See application file for complete search history.

(56) References Cited

U.S. PATENT DOCUMENTS

| | | | |
|---|---|---|---|
| 3,746,814 A * | 7/1973 | Lackey | A61B 18/1402 |
| | | | 606/42 |
| 4,274,553 A * | 6/1981 | Evers | B08B 3/026 |
| | | | 222/146.5 |
| 5,451,735 A | 9/1995 | Worthington et al. | |
| 6,550,356 B1 | 4/2003 | Underwood | |
| 9,849,578 B2 | 12/2017 | Bevins, Jr. et al. | |
| 2002/0049464 A1 | 4/2002 | Donofrio et al. | |
| 2017/0202607 A1 | 7/2017 | Shelton, IV et al. | |
| 2021/0322747 A1 * | 10/2021 | Grassano | A61M 37/0076 |

OTHER PUBLICATIONS

International Search Report and Written Opinion dated Aug. 9, 2021, to PCT Application No. PCT/US21/28257.

* cited by examiner

HAND-HELD POWER TOOL HAVING GRASP-ACTIVATED POWER SWITCH

RELATED APPLICATIONS

This application claims priority to U.S. Provisional Application 63/316,951 filed on Mar. 4, 2022 and is a continuation-in-part to U.S. patent application Ser. No. 17/235,847 filed Apr. 20, 2021, which claims priority to U.S. Provisional Application 63/012,772 filed on Apr. 20, 2020, all of which are fully incorporated herein by reference.

BACKGROUND OF THE INVENTION

Field of the Invention

The present invention relates generally to power switches for hand-held power tools. The invention relates more specifically to a grasp-activated power switch integral to the grip of a hand-held power tool, and most specifically to such a power switch installed on a tattoo machine.

Description of Related Art

The first tattoo machine was derived from the design for an electric pen invented by Thomas Alva Edison in 1877, for which he was awarded U.S. Pat. No. 196,747. That machine used electromagnetic coils for driving a reciprocating pen and needle through paper to create a perforated pattern for autographic printing. In 1891, pioneering tattoo artist Samuel O'Reilly adapted Edison's device for tattooing by adding a tubular handle for delivering ink from an ink reservoir to the perforating needle. For this design O'Reilly was awarded U.S. Pat. No. 464,801.

From then till now, the basic components of a tattoo machine remain essentially unchanged. Tattoo machines all include some type of chassis adapted for hand-held operation that supports a motive force for actuating a linear motor. The motive force may be electromagnetic coils, a rotary electric motor, or a pneumatic motor. A pen coupled to the motive force draws a supply of tattooing ink to inject the ink into the dermis layer of human skin upon each stroke of the motor. Most innovation for tattoo machines has addressed cosmetic desires or ergonomic concerns to give machines a different look and feel.

One such ergonomic advancement has been the provision of a foot pedal for actuating, i.e. switching on or off, the power supply to the motor of a pen-style tattoo machine. While the foot pedal frees the artist's hands from having to actuate the power switch, power cable running from the foot pedal to the tattoo machine motor can often interfere with the artist's freedom of movement. In addition, having to maintain one foot on or near the foot pedal may cause the tattoo artist to assume an awkward position while tattooing, and in general, frequent actuation of the foot pedal is found by many artists to cause discomfort over time.

To overcome that problem, a more recent ergonomic advantage has been the addition of rechargeable battery packs to the chassis of the tattoo machine, made possible by recent improvements in battery technology. These battery packs are typically mounted to the end of the tattoo machine opposite the needle, which advantageously eliminates interference from a tethered power cord. While such battery packs provide the artist with more freedom of movement in one sense, they introduce new problems that arise from placement of the power switch on the battery pack. Because tattooing is both an operation and an art form that requires surgical precision for finely detailed work, the artist must use both hands in cooperation, whereby one hand (the placement hand) carefully stretches and adjusts the skin of a customer being tattooed to achieve an optimal grip about the tattooing site while the other hand (the operating hand) holds and operates the tattoo machine. During a tattooing session, the artist must frequently start and stop power to the tattoo machine for various reasons including cleaning the skin and conserving battery power during short breaks in the action. But to stop or start power, the artist must remove his placement hand from the customer's skin to push the power switch on the battery pack, and then reposition his placement hand to re-achieve the optimal grip. Such action is inefficient, time consuming, and frustrating to the artist.

For the customer, the frequent movement of the artist's placement hand from the surface of her skin back and forth to the power supply switch can be very disturbing, and is in fact an unsound medical procedure because it creates a potentially unsanitary condition. The artist's placement hand, being in close contact with the customer's perforated and bleeding skin, should remain isolated from all other surfaces that can be a potential source of infection.

What is needed is an efficient way for a tattoo artist to start and stop a hand-held battery-powered tattoo machine without having to assume an uncomfortable posture and without having to release his placement hand from the customer's skin.

SUMMARY OF THE INVENTION

The present invention discloses an engineered design for a hand-held power tool having a grasp-activated power switch integrated with the grip portion of the tool. Generally, a grasp-activated power switch according to the present invention allows an operator of the tool to switch power on and off to the tool while the tool is being held in the operator's operating hand, by squeezing the gripping portion of the tool handle with the same operating hand. When installed for example on a tattoo machine, a grasp-activated power switch according to the invention allows a tattoo artist to maintain engagement of his placement hand at the tattooing site on a customer's skin while switching power on and off with his operating hand, without releasing his operating hand from holding the machine. The principles of the present invention may have utility in applications other than tattoo machines, for example, in hand-held power tools such as medical instruments, dental instruments, high-speed drills, etc.

In a basic embodiment of the invention, a grasp-activated power switch for a hand-held power tool includes a rigid but slightly flexible outer shell having an inner conductive layer, and an inner channel having an outer conductive layer and located within the outer shell so that the outer conductive layer is electrically separated from the inner conductive layer. The inner channel is configured for attachment to the power tool at a convenient gripping location. A wireless transmitter is electrically coupled to one of the inner channel or the outer shell, and a battery is electrically coupled to another of the inner channel or the outer shell. The power switch is configured so that a manual grasping force applied to the outer shell causes the outer shell to flex inward, and the inner conductive layer to electrically couple to the outer conductive layer to thereby energize the wireless transmitter by electrically coupling the wireless transmitter to the battery.

In a more detailed embodiment, a grasp-activated power switch of the invention includes a rigid but somewhat flexible outer shell that has both an actuating area and a non-actuating area. These areas are designed so that the manual grasping force when applied to the actuating area electrically couples the inner conductive layer to the outer conductive layer, and when applied to the non-actuating area does not electrically couple the inner conductive layer to the outer conductive layer. This feature allows the operator to manipulate or adjust the power tool while grasping the non-actuating area to avoid undesirably toggling the tool off and on. A more elaborate embodiment of the invention features an inner channel that is generally cylindrical in form, and defines a hollow longitudinal space concentrically aligned within the inner channel. The hollow longitudinal space allows passage therethrough of a moving shaft or other energizeable element of the power tool.

To create the actuating and non-actuating areas on the outer shelf, the invention may include an inner channel having a proximal shelf and a distal shelf, and an outer conductive layer on the inner channel that extends between the proximal shelf and the distal shelf. Both the proximal shelf and the distal shelf are concentrically aligned with the inner channel, and one or both of the shelves has a diameter greater than a maximum width of the outer conductive layer. The difference between the greater diameter and the maximum width of the outer conductive layer defines a gap that electrically separates the inner conductive layer from the outer conductive layer. The non-actuating area lies above one of the two shelves, and the actuating area lies adjacent to the non-actuating area between the two shelves, where the grasping pressure can force the conductive layers into contact.

In another embodiment of the invention, a grasp-activated power switch serves as a handle of a hand-held power tool. The power switch includes an inner channel having an outer conductive layer, and an outer shell surrounding the inner channel, the outer shell having an inner conductive layer, an actuating area, and a non-actuating area. The power switch is configured such that a manual grasping force when applied to the actuating area electrically couples the inner conductive layer to the outer conductive layer, and when applied to the non-actuating area does not electrically couple the inner conductive layer to the outer conductive layer. The power switch may further include a battery and a wireless transmitter electrically coupled to the battery and to one of the inner conductive layer or the outer conductive layer, and configured for wireless coupling to a wireless receiver mounted elsewhere on the power tool. The power switch is configured so that the manual grasping force when applied to the actuating area causes transmission of power within the inner channel.

Another embodiment is a tattoo machine having a linear motor, a battery pack mounted on a proximal end of the machine and configured to energize the linear motor, and a shaft coupled to the linear motor and configured for attachment to a tattoo needle at the distal end of the machine, improved by a handle coupled between the proximal and distal ends of the machine, the handle including a grasp-activated power switch according to the present invention. The grasp-activated power switch includes an outer shell having an inner conductive layer, and an inner channel having an outer conductive layer and located within the outer shell so that the outer conductive layer is electrically separated from the inner conductive layer, wherein the inner channel defines a hollow longitudinal space for passage of the shaft therethrough. The grasp-activated power switch is configured so that a manual grasping force when applied to the outer shell electrically couples the inner conductive layer to the outer conductive layer to switch power off or on to the machine without obstructing movement of the shaft. A wireless transmitter is electrically coupled to one of the inner channel or the outer shell, and a battery is electrically coupled to another of the inner channel or the outer shell, so that the manual grasping force applied to the outer shell energizes the wireless transmitter by electrically coupling the wireless transmitter to the battery. The tattoo machine may further include a wireless receiver configured to receive a wireless signal transmitted by the wireless transmitter, and in response to receiving the wireless signal cause energization of the linear motor by the battery pack.

In yet another alternative embodiment, a grasp-activated power switch directly wired to an internal battery pack for a hand-held power tool is disclosed. By directly wiring the electrical connections internally, an outer shell or grip can be adjusted up and down to provide the maximum comfort to an operator. The adjustable grasp-activated power switch can be particularly useful for small precision hand-held power tools, such as a tattoo machine, where an operator may need to adjust the position of their grip on the tool to maintain precision in the working area. The grasp-activated power switch has an outer shell with an inner conductive layer electrically coupled to a first pin and to a second pin. The tool body within the outer shell has a first conductor and a second conductor, a battery, and a tool motor. The first and second pins extend inward toward the first and second conductors. The tool motor is electrically coupled to one of the first or second conductors and the battery is electrically coupled to the other conductor. Manual grasping force applied to the outer shell results in the first and second pin completing the electrical connection between the first and second conductors such that the tool motor is energized by the battery.

The outer shell is adjustable up and down the tool body between a maximum and minimum position. The first pin and second pin are positioned such that they will always contact the first conductor and second conductor, respectively, when the inner channel is attached between the maximum and minimum positions on the tool body. The inner channel may include threads for threaded engagement with tool body between the maximum and minimum positions.

BRIEF DESCRIPTION OF THE DRAWINGS

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. Component parts shown in the drawings are not necessarily to scale, and may be exaggerated to better illustrate the important features of the invention. Dimensions shown are exemplary only. In the drawings, like reference numerals may designate like parts throughout the different views, wherein:

DETAILED DESCRIPTION OF THE INVENTION

Figure 1:
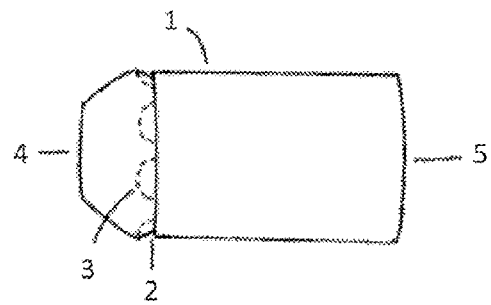
FIG. 1 is a side view of one embodiment according to the invention of a grip for a hand-held power tool having an integral grasp-activated power switch.

The following disclosure presents exemplary embodiments for systems and methods that employ an integral grasp-activated power switch for a hand-held power tool according to the present invention. The grasp-activated power switch allows an operator of the tool to turn the tool on and off by squeezing the grip once to turn on and again to turn off, in toggling fashion. As used throughout this disclosure, the term "grasp-activated" means causing the operation of an electrical switch by a squeezing or clamping action of the operator's hand on a handle or grip portion of the power tool being switched. A grasp-activated action is therefore not accomplished by pushing a button, turning a dial, or by twisting, pushing, or pulling a lever. A grasp-activated action is accomplished by forcing together two opposing sides of a grip or handle by an operator squeezing the grip or handle between his thumb and forefinger.

The present invention applied to tattoo machines improves the comfort, posture, and ease of tattooing for the tattoo artist, and also improves the means for actuating the tattoo machine power supply. The invention allows the artist's operating hand (i.e. the hand that holds the machine) to activate the battery by turning it on and off with a squeeze of the grip for a more seamless tattooing experience. The principles of the present invention may have utility in applications other than tattoo machines, for example, in hand-held power tools such as medical instruments, dental instruments, high-speed drills, etc., especially wherever the tool operator performs high-precision work that requires frequent stopping and restarting of the power tool.

The invention gives tattoo artists the ability to control the power switch of the tattoo machine very easily, when necessary to stop and grab ink, paper towels, or other accessories. The invention is particularly useful when an artist suddenly becomes aware that a supply of ink in an ink cap has run low, because it allows the artist to very easily stop the tattoo machine to prevent the needle from impacting the bottom of the ink cap. Also, about every hour or so, a tattoo artist needs to stop work, stand up, and stretch and with the present invention this can be more easily done. Enhanced power control provided by the grasp-activated grip of the present invention allows the artist to minimize battery power consumption, minimize the likelihood of contaminating the needle, and minimize the risk of accidental injury by puncture from a tattoo needle.

According to the invention, actuation of the grasp-activated switch can connect the tattoo machine motor to the main battery either by directly-coupled wire, or wirelessly by means of an RF or Bluetooth™ transmitter coupled to the grasp-activated switch. Such a wireless transmitter is configured to communicate with a complementary wireless receiver that is coupled to the main battery. The present invention may be integrated into a grip alone, for removable installation on existing tattoo machines or other tools, or the invention may be integrated as part of an entire hand-held power tool system.

FIG. 1 shows a side view of one embodiment according to the invention of a grip 20 for a hand-held power tool having an integral grasp-activated power switch. The grip 20 includes an outer thin plastic wall or shell 1 that provides a gripping surface that allows an operator to manually grasp and control the tattoo machine during operation. A seam 2 is defined between the distal end of the outer shell 1 and a distal end cap 4. The distal end cap 4 is removably attachable to the distal end of shell 1, and may include one or more grooves, protrusions, or indentations 3 that are formed on an outer surface of the end cap 4, as in the example shown, to enable the operator to more easily manually attach or detach the end cap 4 to or from the outer shell 1. An opening 5 at the proximal end of the outer shell 1 provides a means for connecting the grip to a motive force and power supply for energizing the tool.

The outer shell 1 has dual-purpose utility: first, it provides a gripping surface to allow an operator to grasp the tool firmly by one hand, i.e. between thumb and forefinger, while directing and manipulating the tool; and second, it provides a manually operable, or grasp-activated, switch that allows the operator to switch power on and off to the power tool while grasping the tool. In particular, the outer shell 1 is configured with both a non-actuating area and an actuating area. In the embodiments illustrated herein, the non-actuating area occurs at the distal end of the outer shell, and the actuating area occurs away from the distal end of the outer shell, at or near the middle portion of the outer shell, for example. This configuration allows the operator to grasp the outer shell at the non-actuating area and operate the tool without causing the tool to switch on or off, or slightly adjust his grip and grasp the outer shell at the actuating area where he can switch power to the tool on or off by gently squeezing the outer shell 1 between his thumb and forefinger.

To enable the dual-purpose utility of the outer shell 1, the outer shell 1 is preferably formed from a rigid but slightly resilient material such as a thermoplastic—ABS, nylon, polycarbonate, polyethylene, etc.—or from a thin metal sheet such as steel or aluminum that will allow for slight flexing. In another embodiment, a hard synthetic rubber may be used to form the outer shell. When used for tattoo machines or on medical or dental instruments, an advantage provided by the invention is the option to design the outer shell 1 to be disposable, for sanitary purposes. Thus, longevity of service life may not be an essential design basis, so that less expensive materials of construction can be selected for the outer shell.

Figure 2:
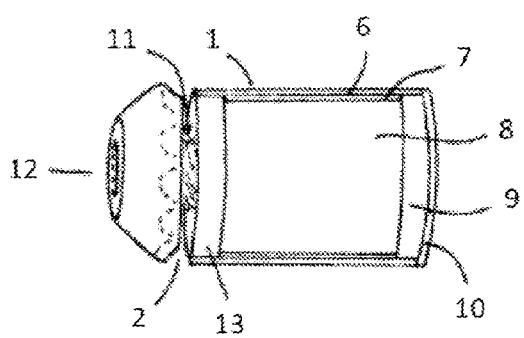
FIG. 2 is a transparent and partially exploded side view of the grip of FIG. 1.

FIG. 2 shows a transparent and partially exploded side view of the grip 20. In this view, the distal end cap 4 is shown partially detached from the grip 20 to reveal threads 11 that illustrate one possible means for removably attaching the distal end cap 4 to the grip 20. The transparent view reveals that the outer shell 1 has an inner conductive layer 6 disposed onto its inner surface. In the embodiment shown herein, the outer shell 1 is generally cylindrical, and the inner conductive layer 6 also forms a generally cylindrical inner wall. The inner conductive layer may be the inner surface of an outer shell 1 that is composed of metal. Or the inner conductive layer 6 may be a thin metal sheet material curved into a cylindrical form and attached to a non-metallic inner surface of the outer shell 1, or the inner conductive layer 6 may be a pre-formed cylindrical metal pipe, or it may be a portion of a conductive metal sheet, pipe, or other material attached to a non-conductive material that forms part or all of the outer shell 1.

The grip 20 also includes an inner channel 8 that is concentrically aligned with the outer shell 1. A hollow longitudinal space 22 runs through the center of the inner channel 8 from proximal opening 5 to distal opening 12. The inner channel 8 may also be generally cylindrical in form, and has an outer conductive layer 21 on its outer surface that is displaced from the inner conductive layer 6 by a gap 7. Gap 7 may be on the order of about 0.036 inches in width, although greater and lesser such widths are certainly possible within the scope of the invention. And while the embodiment of grip 20 disclosed herein has a generally cylindrical form, with generally cylindrical conductive layers 6 and 8, other geometric configurations are possible within the scope of the invention that maintain a gap 7 of a desired width. The desired width of the gap 7 is a distance sufficient to prevent electrical current flow across the gap when the grip is not being squeezed when the tool is electrically energized, but that also provides good electrical contact between conductive layers 6 and 21 when the actuating area of outer shell 1 of the electrically energized tool is being squeezed with manual force.

To maintain the form and integrity of the grip 20, the inner channel 8 is formed from a rigid material that is generally not flexible and will not deform under a manual gripping force. Materials such as metal or hard plastic are suitable for forming the inner channel 8. To create the non-actuating and actuating areas of the outer shell 1, a proximal shelf 9 and a distal shelf 13 are formed on respective ends of the inner channel 8. The shelves 9 and 13 are similarly formed from rigid materials, and may be integral to the inner channel 8, or rigidly attached thereto. The outer shell 1 spans over both the proximal shelf 9 and the distal shelf 13. Preferably, shelves 9 and 13 are made from a dielectric material, with one or both of the shelves 9 or 13 having a conductive outer surface. In the embodiments shown herein, the proximal shelf 9 has a dielectric surface and the distal shelf 13 has a conductive surface. When the grip 20 is in the "shelf" position, that is, resting on a shelf or otherwise in a condition not being grasped or squeezed by an operator's hand, the conductive surface of the distal shelf 13 is electrically separated from the outer conductive layer 21 on the inner channel 8. Also while in the shelf position, the inner conductive layer 6 of the outer shell 1 forms a conductive bridge over shelves 9 and 13. In the shelf position, the inner conductive layer 6 may contact the conductive surface of the distal shelf 13 and the dielectric surface of shelf 9, but does not contact the outer conductive layer 21, being separated therefrom by the gap 7. The non-actuating area of the outer shell 1 therefore occurs at or near the distal end of the outer shell, where pressure between the operator's thumb and forefinger will force the inner conductive layer 6 against the conductive surface of the distal shelf 13, but not deform the outer shell 1 to cause any part of the inner conductive layer 6 to close the gap 7 and make contact with the outer conductive layer 21 of the inner channel 8. Accordingly, the actuating area of the outer shell 1 occurs a short distance away from the distal end of the outer shell 1 at an intermediate location between the proximal shelf 9 and distal shelf 13, where pressure between the operator's thumb and forefinger will slightly deform the outer shell 1 and force the inner conductive layer 6 into electrical contact with the outer conductive layer 21 of the inner channel 8, thereby closing the grasp-activated switch.

The inner channel 8 may include complementary means for removably receiving the distal end cap 4. In this example, such receiving means comprises female threads formed on the distal end of the inner channel 8 and sized to engage with male threads on the distal end cap 4. An opening 12 is defined through the distal end cap 4, to accommodate the distal end or working element of the power tool, e.g., a saw blade, drill bit, or the needle end of a tattoo machine. Opening 12 passes all the way through the longitudinal center of grip 20 to the proximal opening 5 to allow the grip 20 to be installed on the power tool and to allow the working element at the distal end of grip 20 to be coupled to the motor of the power tool at the proximal end of grip 20.

Figure 3:
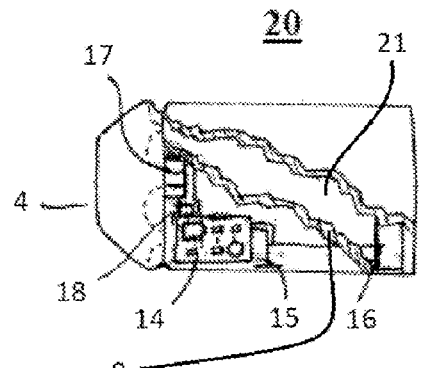
FIG. 3 is a partially cutaway side view of the grip of FIG. 1.

FIG. 3 shows a partially cutaway side view of the grip 20. This view reveals electronic components that are mounted to the inner channel 8 and that make up a portions of the electrical circuit of the grasp-activated power switch. These components include a circuit board, a battery 17, and wiring 15, 16, 18. The circuit board includes an RF transmitter 14. The battery 17 provides power to the transmitter 14. Battery 17 may consist of multiple batteries ganged in series and/or parallel to achieve a desired voltage. Each such battery may be lithium ion type or another known type of battery technology, disposable or rechargeable. In one example, battery 17 consists of a single 3.7-V lithium ion disposable battery. In another example, battery 17 consists of three 1.5-V batteries.

In FIG. 3, the battery 17 is mounted to the distal shelf 13. In other embodiments, the battery 17 may be mounted to the distal end cap 4, to the outer shell 1, or to another location on grip 20. Wiring 15 electrically couples the positive terminal of the transmitter 14 to the outer conductive layer 21 of the inner channel 8. Wiring 16 electrically couples the positive terminal of battery 17 to the inner conductive layer 6 of the outer shell 1. Wiring 18 connects the negative terminal of the transmitter 14 to the negative terminal of battery 17 to complete the circuit, so that when a sufficient manual grasping force squeezes grip 20 to make electrical contact between the inner conductive layer 6 and the outer conductive layer 21, the grasp-activated switch closes and as a result transmitter 14 is energized by the battery 17. See FIG. 16.

When the transmitter 14 is energized, it transmits an on/off signal or pulse to a complementary receiver 24 that is mounted on or near the main power supply for energizing the motor of the hand-held tool. For example, where the hand-held tool is a tattoo machine, the main power supply may be a main battery pack mounted at the proximal end of the machine. In this way the main battery back is configured for wireless communication with the transmitter 14. When the receiver 24 receives the on/off signal, it causes a switch at the output of the main battery pack to change state, using any of numerous flip-flop type logic circuits well known in the electrical engineering arts. That is, if the main battery pack switch was off when the on/off signal is received, it changes state to on, and if the battery pack switch was on when the on/off signal is received, it changes state to off. In this manner an operator of the hand-held tool using a grip 20 according to the present invention can toggle power off and on to the motor of the tool by momentarily squeezing the actuating area of outer shell 1 with his operating hand that is already grasping the grip 20.

One advantage of using the combination wireless transmitter 14 and receiver 24, rather than hard-wiring the grasp-activated switch to the terminals of main power supply, is to provide a disposable part that can be easily installed onto the hand-held tool with no effect on the wiring. For example, after a tattooing session, the operator can disconnect the end cap 4, pull the grip 20 (consisting of the shell 1 and inner channel 8) off the distal end of the tool, and discard the grip 20 as medical waste. Another advantage of the wireless switch is to avoid having to run wiring in close proximity to moving parts of the tool, which is especially useful when using the grasp-activated switch of the present invention as an after-market modification to a commercially available tool. In other embodiments of the invention, however, the grasp-activated switch may be hard-wired to the main power supply of the tool, to reduce the overall manufacturing cost of the grip, and possibly increase reliability by eliminating the need for the battery 17.

Figure 4:
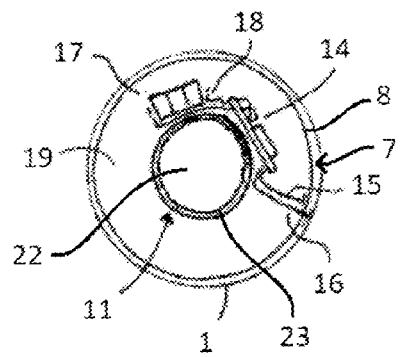
FIG. 4 is a distal end view of the grip of FIG. 1 with cap portion removed.

FIG. 4 shows a distal end view of the grip 20 with distal end cap 4 removed. This view shows wiring 18 that couples the negative terminal of battery 17 to the negative node of the transmitter 14. In one embodiment, the grip 20 may include a dielectric core 19 between the inner channel 8 and the hollow longitudinal space 22 that runs through the center of the inner channel 18 from proximal opening 5 to distal opening 12. The dielectric core 19 adds strength and rigidity to the grip, and may be made from a resilient material to assist the grip in restoring itself to original form when an operator's grasping force is released. In one embodiment, the dielectric core 19 may be formed from an epoxy. In another embodiment, the dielectric core 19 may comprise silicone. In another embodiment, the dielectric core may provide structural support and insulation to one or more electrical components of the grip 20. In one example, the transmitter 14, battery 17, and associated wiring and/or circuit boards may be embedded within the material of the dielectric core during manufacture while the core is in liquid or gel form prior to setting.

The hollow longitudinal space 22 runs through an interior wall 23 that is concentrically aligned with the longitudinal axis of the inner channel 8. Space 22 is configured to allow the working end of the hand-held tool to pass through the grip 20 unobstructed. The interior wall 23 is formed from a rigid material configured to engage one or more bearings or other components that support a shaft of the motor of the hand-held tool. The interior wall 23 has sufficient strength to resist deformation when an operator squeezes the outer shell 1, so that tool operation is unobstructed during the transition of power from off to on or vice versa.

Figure 5:
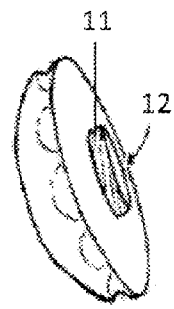
FIG. 5 is a perspective view of the cap portion of the grip of FIG. 1.

FIG. 5 shows a perspective view of the distal end cap 4 of the grip 20, to illustrate threads 11 that surround the opening 12. The threads 11 may be configured to engage complementary threads formed on the distal end of the interior wall 23. The end cap 4 may assume a variety of shapes, depending on the configuration of the working end of the tool. Ideally, when the end cap 4 is fully engaged to the interior wall 23, a tight seal is formed at seam 2 to insulate the electronic components from contamination.

Figure 6:
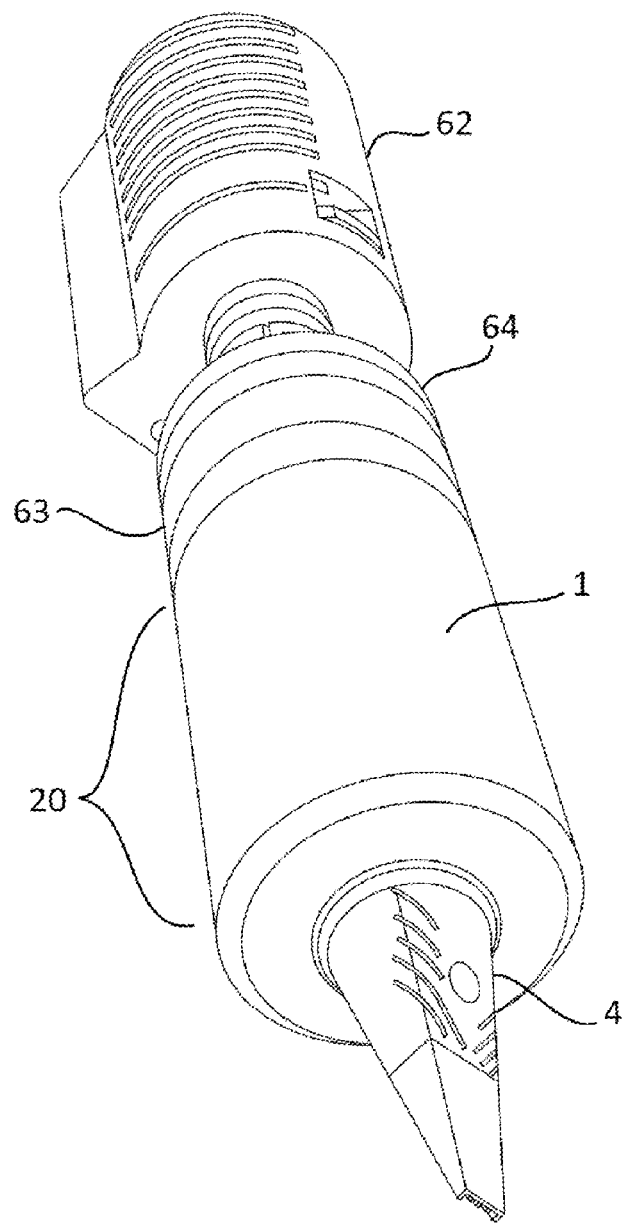
FIG. 6 is a perspective view of another embodiment according to the invention of a tattoo machine having an integral grasp-activated power switch.
Figure 7:
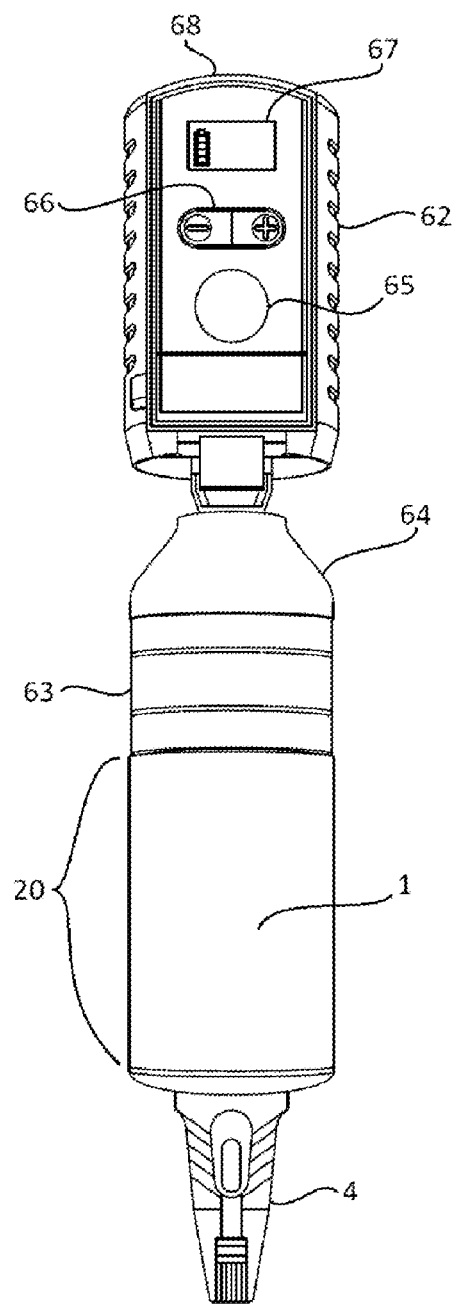
FIG. 7 is a frontal view of the tattoo machine of FIG. 1.
Figure 8:
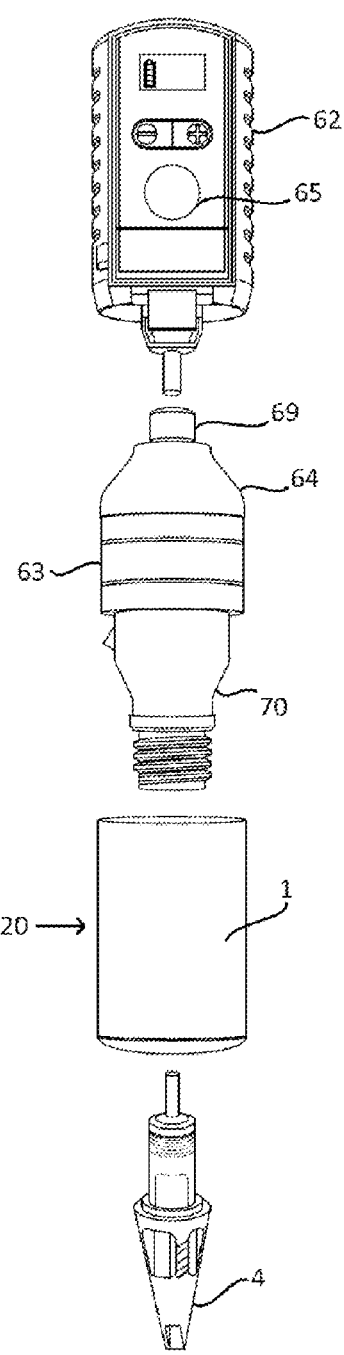
FIG. 8 is an exploded frontal view of the tattoo machine of FIG. 1.

FIG. 6 shows a perspective view of another embodiment according to the invention. In this embodiment, the hand-held tool that bears the grasp-activated power switch is a tattoo machine 60. Tattoo machine 60 is a commercially available machine that is modified by installing a grip 20 of the present invention as an after-market modification. An outer shell 1 of the grip 20 is shown in the figure. A battery compartment 62, also modified according to the invention, is connected to the proximal end of the tool 60. An end cap 4 is attached to the distal end of the tool 60, to protect a reciprocating tattoo needle driven by a linear motor that is enclosed within a motor casing 64. A grip 63, provided by the original tattoo machine manufacturer, allows a user to grasp the machine 60 while operating it; however, grip 63 is a static device that does not provide a grasp-activated switch. FIG. 7 shows a frontal view of the tattoo machine 60. Several additional optional features are shown on the battery compartment 62. These include a manual on/off pushbutton 65, a voltage up/down toggle switch 66, an LED display 67, and a lid 68. FIG. 8 shows an exploded frontal view of the tattoo machine 60. This view reveals the proximal end of the linear motor 69 that lies within the motor casing 64, and also the distal end 70 of the machine as provided by the original tattoo machine manufacturer.

Figure 9:
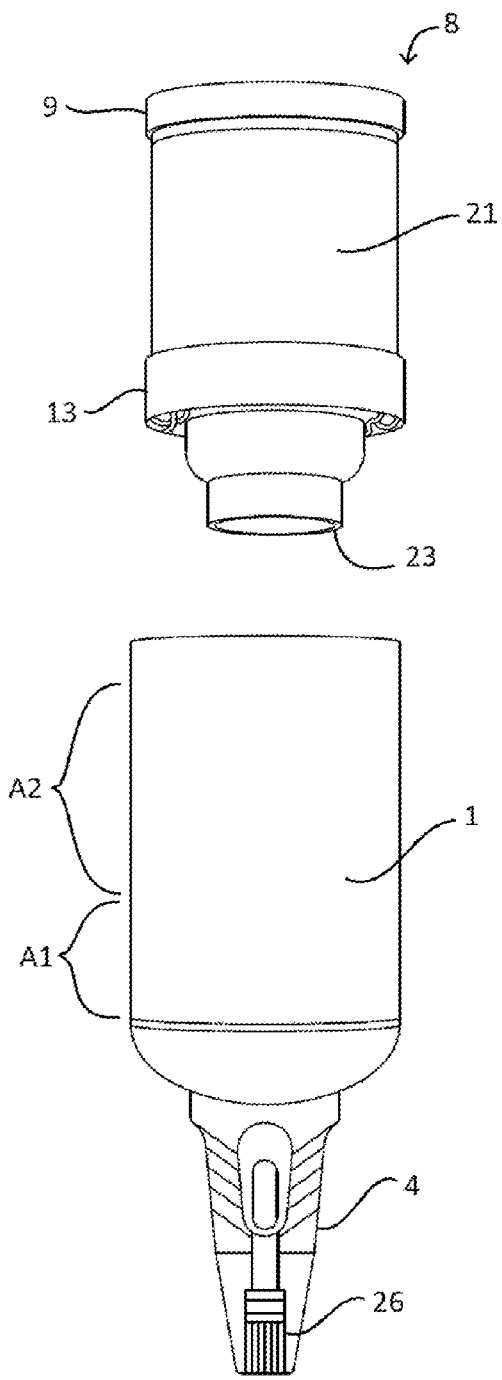
FIG. 9 is an exploded frontal view of the distal end of the tattoo machine of FIG. 1, showing an outer shell and inner channel.

FIG. 9 shows an exploded frontal view of the distal end of the tattoo machine 60. This view illustrates two main components of the invention that are used in the modification of machine 60—the outer shell 1 and the inner channel 8. Threading on interior wall 23 may be used by an operator to adjust the length of protrusion of a tool element, such as a tattoo needle 26, beyond the distal end of the end cap 4. While making this adjustment, with the machine fully assembled as shown in FIG. 7, the operator may grasp the outer shell 1 of grip 20 at its non-actuating area A1 and press the outer shell 1 against the distal shelf 13, then rotate the end cap 4 with respect to the grip 20. In this manner, the adjustment can be made without switching the machine on or off.

Figure 10:
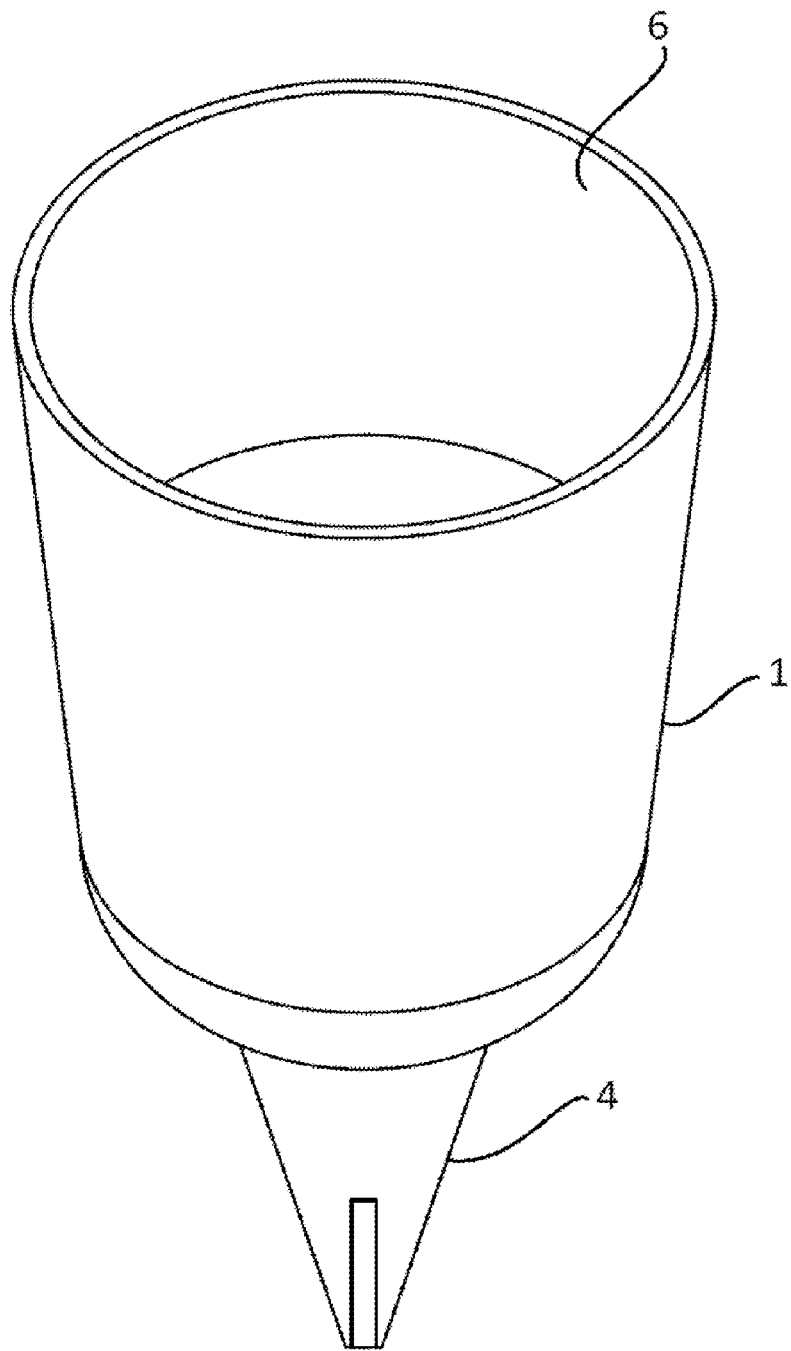
FIG. 10 is a perspective view of the outer shell of a tattoo machine having an integral grasp-activated power switch according to the invention.
Figure 11:
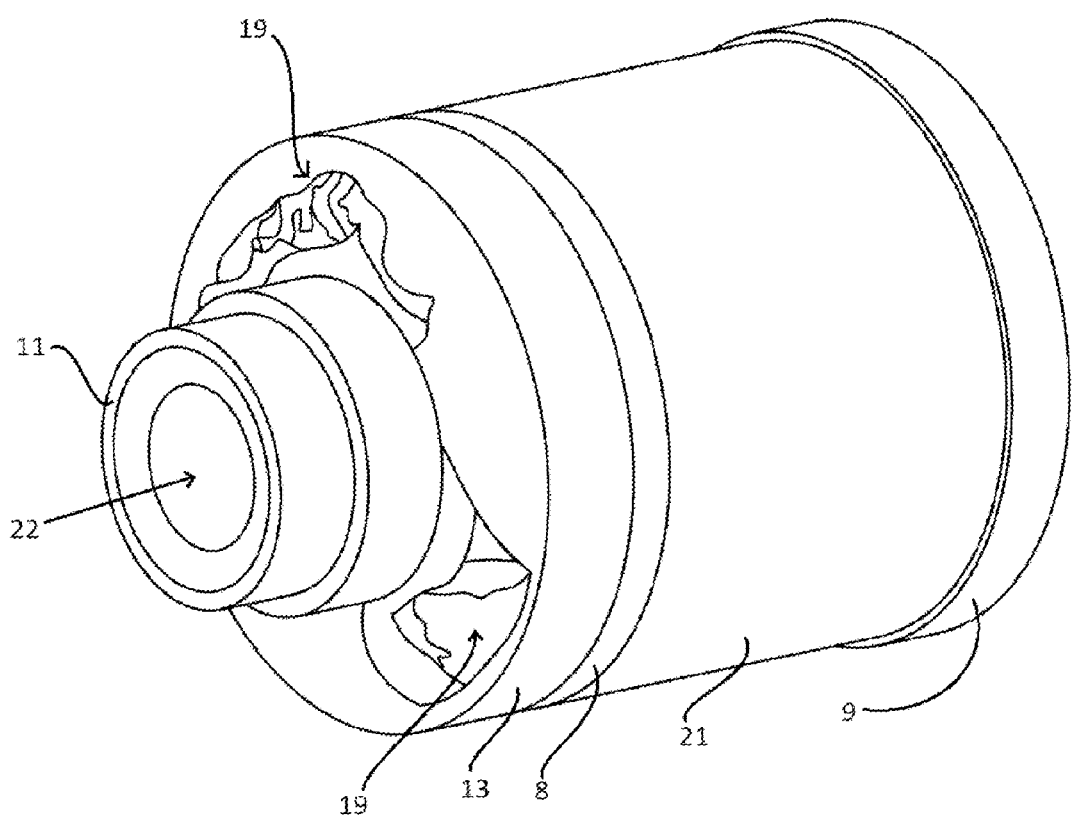
FIG. 11 is a distal end perspective view of an inner channel of a tattoo machine having an integral grasp-activated power switch according to the invention.
Figure 12:
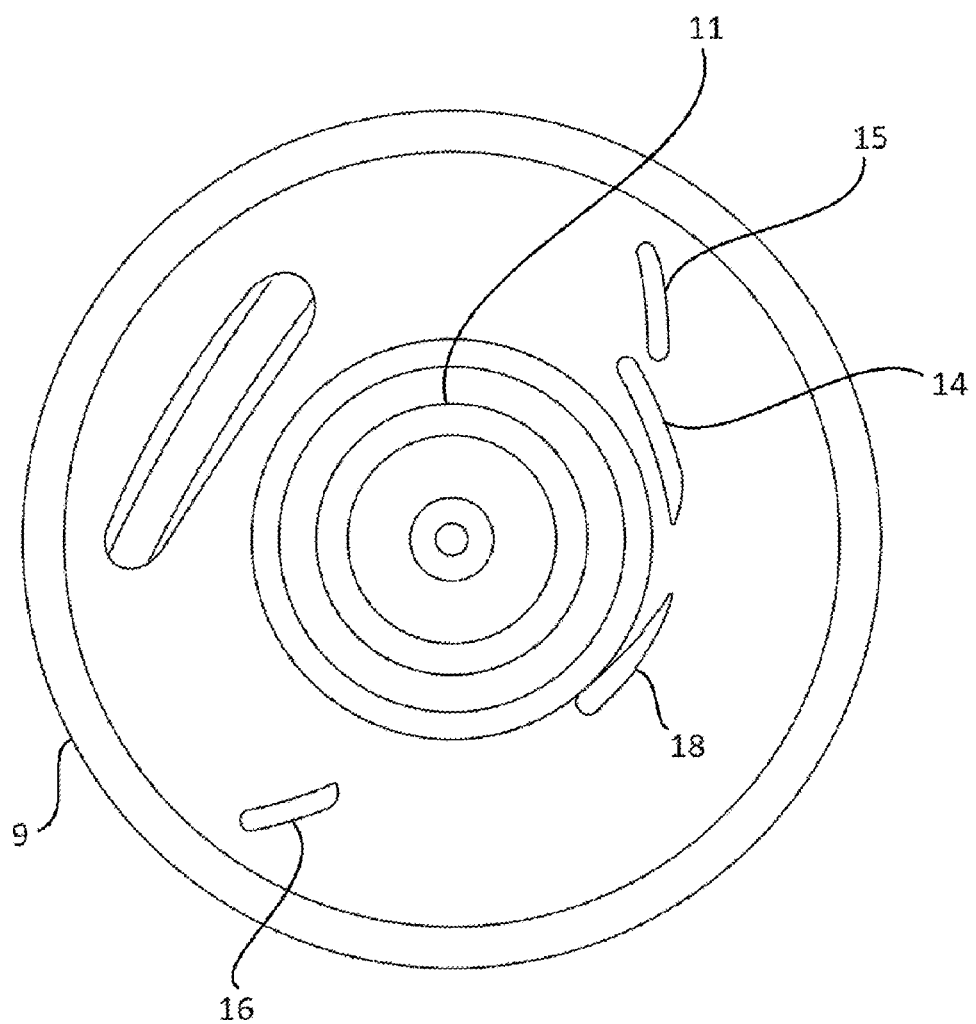
FIG. 12 is a proximal end view of an inner channel for one embodiment of a grasp-activated power switch according to the invention.

FIG. 10 shows a perspective view of the outer shell 1 of the tattoo machine 60. The inner conductive layer 6 is shown on the inner surface of the outer shell 1. FIG. 11 shows a distal end perspective view of an inner channel of a tattoo machine having an integral grasp-activated power switch according to the invention. The dielectric core 19 made from epoxy or silicone fills the void between inner channel 8 and the hollow longitudinal space 22. Various electronic components and wiring may be embedded within the core 19. FIG. 12 shows a proximal end view of an embodiment of an inner channel 8.

Figure 13:
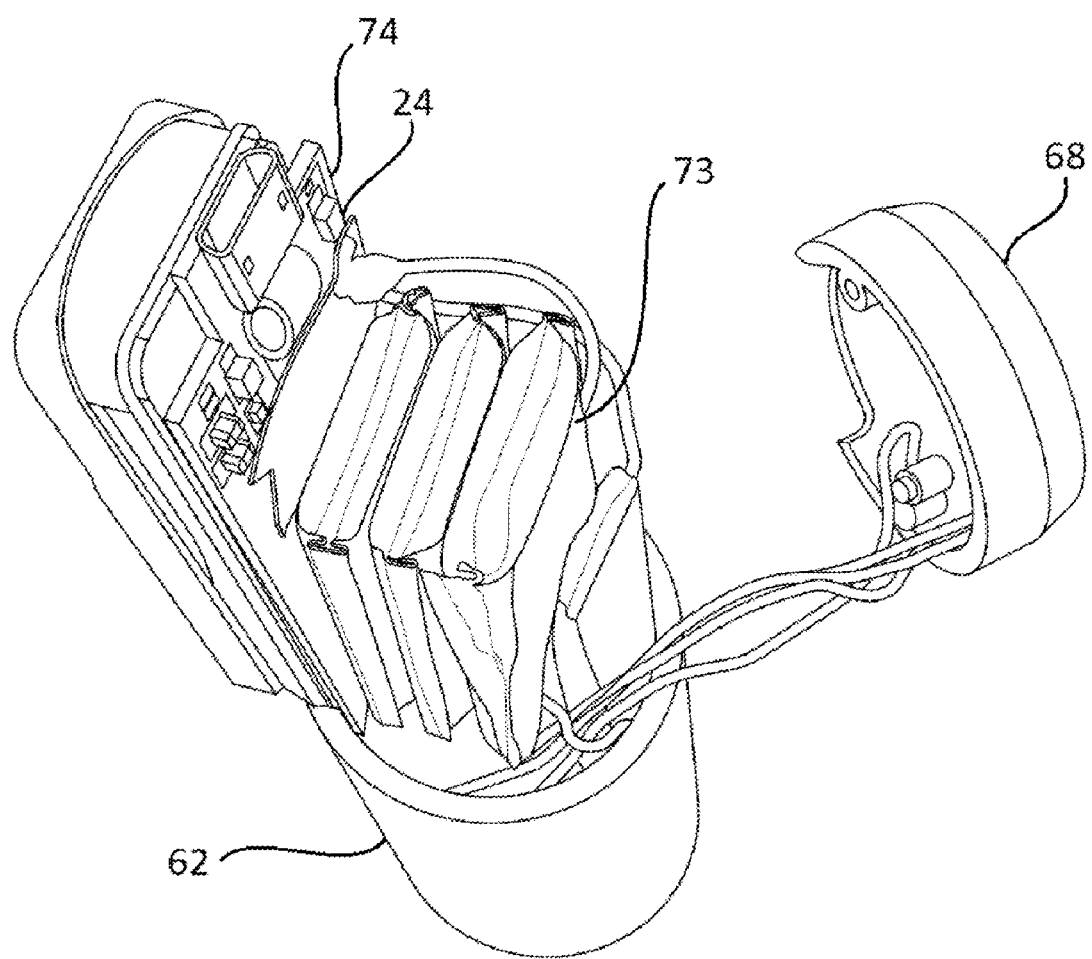
FIG. 13 is a perspective view of one embodiment of a battery pack for a tattoo machine having an integral grasp-activated power switch according to the invention.

FIG. 13 is a perspective view of one embodiment of a battery pack 62 for a tattoo machine having an integral grasp-activated power switch according to the invention. Battery pack 62 includes one or more individual batteries 73 arranged as a pack in a series or parallel configuration to achieve a desired voltage needed to drive the machine's DC motor, usually 7.5V to 8.5V for a tattoo machine. The manual on/off switch 65 is bypassed so that the on/off switching operation can be performed by an electric circuit provided on a circuit board 74 that is mounted within the battery pack 62. The circuit board 24 includes a receiver 24 that is configured to receive and respond to an RF signal from the transmitter 14 that is mounted to the grasp-activated switch 20. Other components on circuit board 24 are shown in the circuit diagram of FIG. 15.

Figure 14:
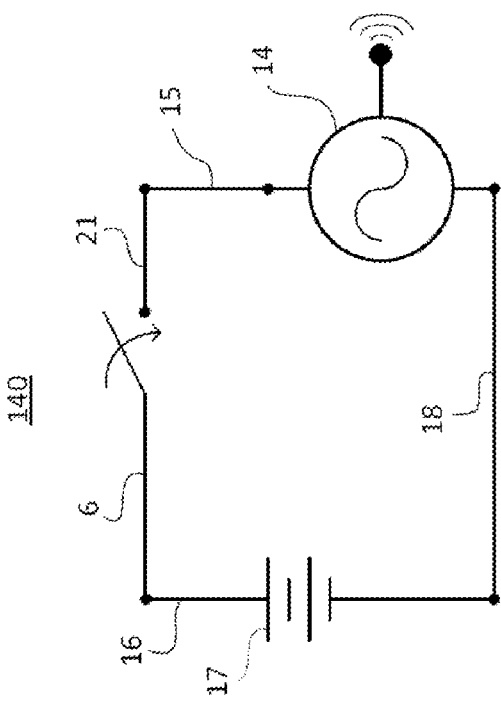
FIG. 14 is a circuit diagram showing electrical connections in the grip area for one embodiment according to the invention for a hand-held power tool having an integral grasp-activated power switch.

FIG. 14 is a circuit diagram 160 that shows typical electrical connections in the grip area for one embodiment according to the invention for a hand-held power tool, such as a tattoo machine, having an integral grasp-activated power switch. Wiring 16 connects the positive terminal of battery 17 to the inner conductive layer 6. The outer conductive layer 21 is connected by wiring 15 to the positive terminal of the RF transmitter 14. The negative terminal of transmitter 14 is connected by wiring 18 to the negative terminal of battery 17. When an operator squeezes the actuating area of the outer shell 1, the inner conductive layer 6 is pressed into electrical contact with the outer conductive layer 21 to close the switch and complete the circuit. This action energizes the transmitter 14, which sends a momentary RF pulse wirelessly to receiver 24 that is mounted in the battery pack on the proximal end of the tool. The operator need only squeeze the grip momentarily to switch the power on or off to the tool. A subsequent squeeze will cause the tool to change state again, either from on to off or off to on.

Figure 15:
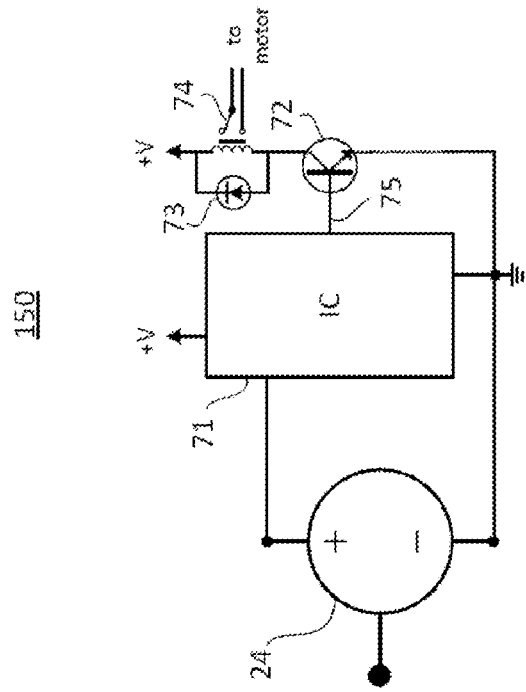
FIG. 15 is a circuit diagram showing electrical connections in the battery pack area for one embodiment according to the invention for a hand-held power tool having an integral grasp-activated power switch.

FIG. 15 is a circuit diagram showing electrical connections in the battery pack area for one embodiment of a hand-held power tool, such as a tattoo machine, having an integral grasp-activated power switch. The RF receiver 24 is configured to receive and respond to the RF pulse transmitted by transmitter 14. The response of the receiver 24 is to generate a pulse, such as a voltage spike of about 5 volts, across its terminals using methods known in the art. The pulse is fed to an input pin of an integrated circuit (IC) 71 that is configured as a toggle switch flip-flop. For example, an IC 4017 may be used for this purpose, by connecting pin #4 to pin #15 so that each successive pulse at the input toggles the output between 0 and +5V. The toggling output pin is coupled to the base 75 of a transistor 72 configured to behave as a solid state switch. Transistor 72 will therefore change state with each successive pulse, alternately enabling and disabling current flow to a relay 74 that is magnetically coupled to a normally open switch. When current flows through transistor 72, relay 74 is energized, closing the switch that provides power from batteries 72 to the tool motor, such as linear motor 69 described in a previous embodiment. When current through transistor 72 is cut off, relay 74 de-energizes and the switch opens to stop the motor. Circuits 140 and 150 can thereby perform the same function as the manual on/off pushbutton switch 65, to allow an operator to toggle the tool on and off. But unlike switch 65, an operator using the present invention can toggle the power by momentarily squeezing the grip.

Figure 16:
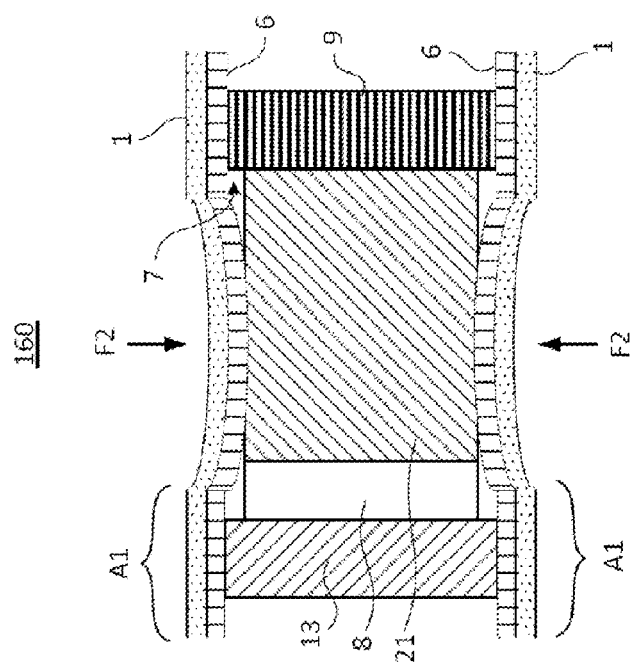
FIG. 16 is a cross-sectional view of one embodiment according to the invention for a grasp-activated switch when a grasping force is applied to a non-actuating area.
Figure 17:
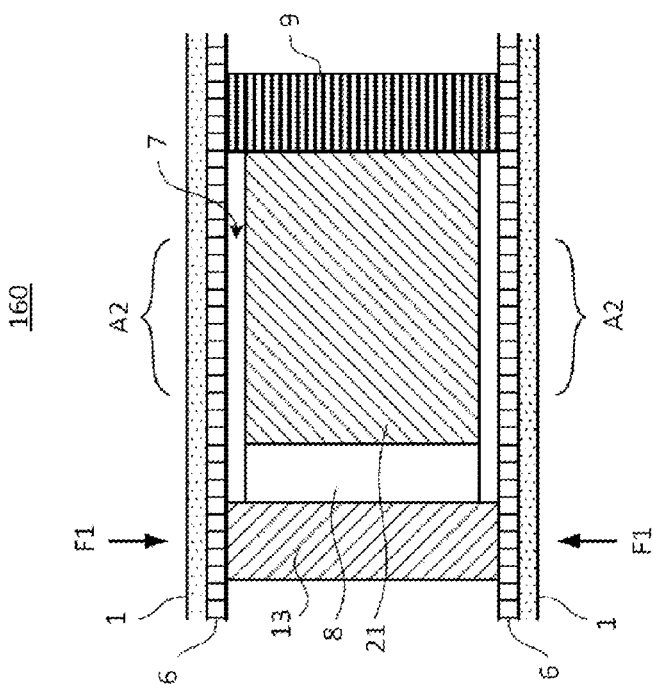
FIG. 17 is a cross-sectional view of one embodiment according to the invention for a grasp-activated switch when a grasping force is applied to an actuating area.

FIGS. 16 and 17 are a cross-sectional views of one embodiment according to the invention for a grasp-activated switch 160. Switch 160 is similar in form and function to the grasp-activated switch described within grip 20 as shown in FIGS. 1-5. FIG. 16 illustrates the configuration of switch 160 when a grasping force F1 is applied to a non-actuating area A1. FIG. 17 illustrates the configuration of switch 160 when a grasping force F2 is applied to an actuating area A2. In general, the non-actuating area A1 of the switch occurs at the distal end of the assembly on and about the area where the outer shell 1 covers the distal shelf 13. In one embodiment, the non-actuating area occurs approximately along the "distal third" of the grip. The actuating area A2 of the switch occurs along an area proximally adjacent to area A1, along the middle area of the outer shell 1. In one embodiment, the actuating area A2 occurs along about twice the length of the non-actuating area A1. In other embodiments, the size, length, and location of areas A1 and A2 may vary, depending on tool type, size and other design considerations. In another example, the proximal shelf 9 may be made conductive and separated from the outer conductive layer 21, and the distal shelf 13 may be made non-conductive, so that the distal-to-proximal locations of areas A1 and A2 are reversed, with A2 located on the distal side of A1.

In FIG. 16, a grasping force F1 is applied to the non-actuating area A1. This action has no effect on the grasp-activated switch, and so the switch remains open, with gap 7 separating inner conductive layer 6 from outer conductive layer 21. An operator may grasp the outer shell 1 in this manner while operating or adjusting the tool.

In FIG. 17, the operator changes the state of the grasp-activated switch by momentarily adjusting his grip on the outer shell 1 to place his thumb and forefinger within the actuating area A2 and squeezing the outer shell 1 with a quick, firm pulse. This action drives the inner conductive layer 6 across the gap 7 into electrical contact with the outer conductive layer 21, thereby completing the circuit, e.g. as shown by the switch in circuit 140. As described in the context of circuits 140 and 150, the grasping pulse of the operator at area A2 causes a change of state in the operation of the power tool, from on to off or from off to on.

Figure 18:
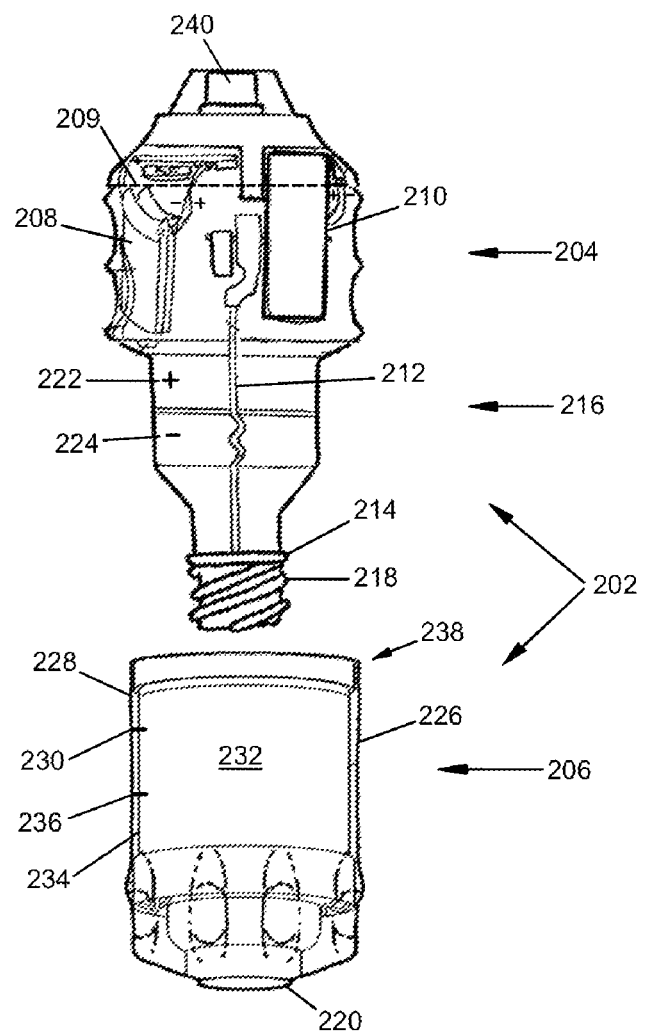
FIG. 18 is an exploded transparent side view of an alternative embodiment according to the invention of a tattoo machine having an integral height adjustable grasp-activated power switch.

FIG. 18 is an exploded transparent view of an alternate embodiment according to the present invention of a tattoo machine 200 having a height-adjustable grasp-activated power switch 202. The tattoo machine 200 has a tool body 204 and an attachable grip 206. The tool body encloses a battery 208 electrically coupled to a tool motor 210. (Note, the dotted line at 209 is meant to demonstrate a wired connection between the battery 208 and the tool motor 210.) A power attachment end 240 of the tool body 204 is configured to receive an external battery pack 62 or be wired directly into a power source, e.g., a conventional cord and plug. Connection between the power attachment end 240 of the tool body 204 and the external battery pack 62 can be accomplished through conventional means. The external battery pack 62 is one source of power for the tool motor 210 of the present embodiment. Alternatively, a convention cord and plug (not shown) can be used to provide power to the tool motor 210. The tool motor is mechanically coupled to a tattoo needle plunger 212 configured to deliver tattooing ink to a working surface, e.g., the surface of the skin being tattooed. The distal end 214 of the tool body 204 is configured to removably attach the grip 206 so that an actuating area 216 of the tool body is completely encompassed by the grip, which position can be adjusted up and down the actuating area. In preferred embodiments, the distal end 214 of the tool body 204 includes male threads 218 configured for threaded engagement with corresponding female threads positioned within the distal end 220 of the grip 206.

The tool body 204 also has a first conductor 222 and a second conductor 224 that are formed as integral parts of the actuating area 216 of the tool body 204. The first conductor 222 is electrically separated from the second conductor 224. The tool motor 210 is electrically coupled to either the first conductor 222 or the second conductor 224 and to the battery 208. The other of the first conductor 222 or the second conductor 224 is electrically coupled to the battery 208 to form an open circuit. The grip 206 has an outer shell 226 that is electrically separated from the tool body 204. The outer shell 226 has an inner conductive layer 228 that is electrically coupled to a first pin 230 and to a second pin 236. The first pin 230 and the second pin 236 extend inward towards the first conductor 222 and second conductor 224 on the tool body 204. The outer shell 226 has a preferably hollow internal channel 232. The first pin 230 and the second pin 236 are configured to complete the electrical connection between the first conductor 222 and the second conductor 224 when a manual grasping force is applied to the actuating area 216 when the grip 206 is engaged to the tool body 204. This energizes the tool motor 210. To de-energize the tool motor 210 when it is desired to shut off the tattoo machine 200, an operator reapplies the grasping force to the actuating area 216.

Figure 19A:
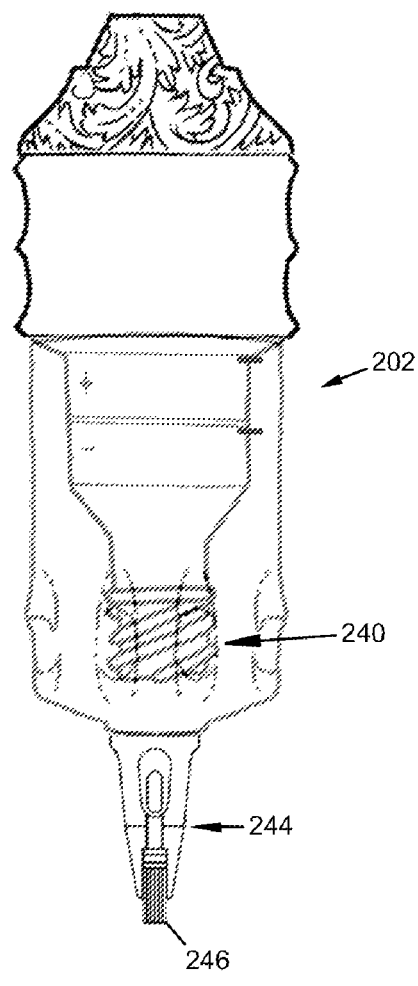
FIGS. 19A-19B are partially transparent side views of a tattoo machine showing the height adjustability of the height-adjustable grasp-activated power switch of FIG. 18
Figure 19B:
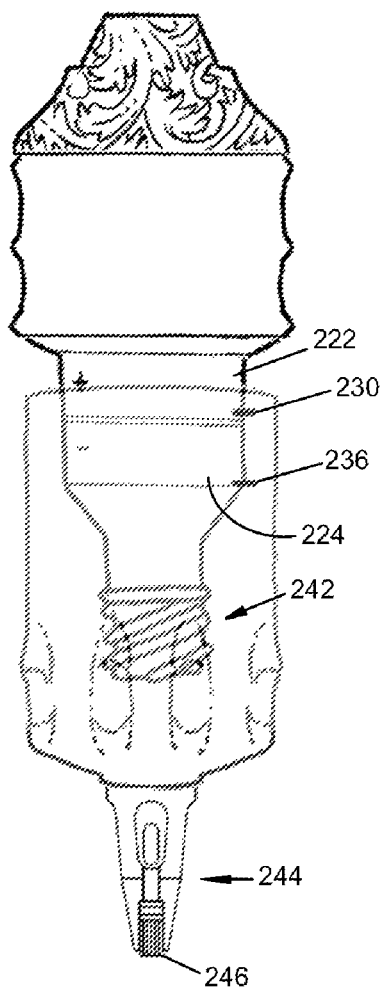

FIGS. 19A and 19B are partially transparent views of the tattoo machine 200 demonstrating the adjustable positioning of the grasp-activated power switch 202 on actuating area 216 of the tool body 204. A needle cap 244 is attached to the distal end 220 of the grip 206 and provides cover for a tattoo needle 246 that is coupled to the needle plunger 212. By adjusting the grip 206 up or down relative to the tool body 204, an operator can now readily control the length of the tattoo needle 246 protruding out of the needle cap 244 which defines the depth the needle 246 can penetrate the working surface, e.g., surface of the skin being tattooed. Depth of penetration for a tattoo needle is an important feature that needs to be controlled by the tattoo artist Different tattooing methods require different needle penetration depths. Further, regardless of the method, a tattoo artist will be required to periodically adjust the needle penetration depth based on which part of the body the artist is currently tattooing, e.g., bony areas where the skin is tight versus more fatty/muscular areas where the skin is looser. To achieve this adjustability, the actuating area 216 has a maximum attachment position 240 for attaching the grip 206 to the tool body 204 and a minimum attachment position 242. The grip 206 is designed so that the first pin 230 and the second pin 236 maintain the ability to contact the first conductor 222 and the second conductor 224 when the grip 206 is attached to the tool body 204 between the maximum attachment position 240 and the minimum attachment position 242 of the actuating area 216. In the illustrated embodiment, the maximum attachment position 240 is achieved when the female threads at the distal end 220 of the grip 206 are fully engaged with the male threads 218 at the distal end 214 of the tool body 204. The minimum attachment position 242 is achieved when the female threads at distal end 220 are partially engaged with the male threads 218. The partial threaded connection positions the grip 206 a distance forward from the tool body 204 such that the needle cap 244 covers more of the needle 246 thereby decreasing the depth of penetration.

Figure 20:
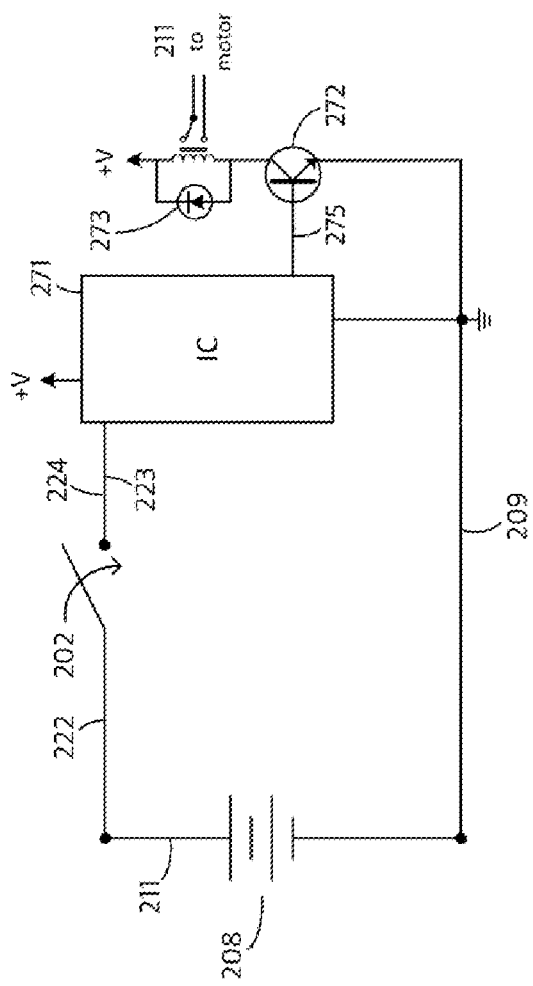
FIG. 20 is a circuit diagram showing electrical connections of the height adjustable grasp-activated power switch of FIG. 18.

FIG. 20 is a circuit diagram showing electrical connections for the tattoo machine 200 of FIGS. 18-19B. Wiring 211 connects the positive terminal of the battery 208 to the first conductor 222. The second conductor 224 is connected by wiring 223 to the positive terminal of the integrated circuit (IC) 271. The integrated circuit 271 can be similar to integrated circuit 71 described above, i.e., configured as a toggle switch flip-flop. Wiring 209 grounds the negative terminal of the integrated circuit 271 with the negative terminal of the battery 208. When the power switch 202 is grasped by an operator, the first and second pins 230, 236 contact the first conductor 222 and second conductor 224 to close the circuit generating a pulse that is fed as an input signal to the integrated circuit 271 which toggles the output between, for example, 0 and +5V. The toggling output pin is coupled to the base 275 of a transistor 272 configured to behave as a solid state switch. Transistor 272 thus changes state with each successive pulse, alternately enabling and disabling current flow to a relay 274 that is magnetically coupled to a normally open switch. When current flows through transistor 272, relay 274 is energized, closing the switch that provides power from batteries 273 to the tool motor 210. When current through the transistor 272 is cut off, relay 274 de-energizes and the switch opens to stop the motor. The batteries 273 can an external, rechargeable battery pack, similar to the battery pack 62 previously described.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A grasp-activated power switch for a hand-held power tool, comprising:
    an outer shell having an inner conductive layer electrically coupled to a first pin and a second pin extending inward toward a tool body;
    the outer shell is configured for attachment to the tool body, wherein the outer shell is electrically separated from the tool body, the tool body having a first conductor, a second conductor, a battery, and a tool motor;
    the tool motor is electrically coupled to one of the first conductor or the second conductor and to the battery;
    the battery is electrically coupled to the other of the first conductor or the second conductor;
    whereby a manual grasping force applied to the outer shell causes the first pin and the second pin to complete an electrical connection between the first conductor and the second conductor thereby energizing the tool motor.

2. The grasp-activated power switch for a hand-held power tool of claim 1, wherein the outer shell is attachable to the tool body between a maximum position and a minimum position, wherein the first pin and the second pin contact the first conductor and the second conductor when the outer shell is attached to the tool body between the maximum and minimum positions.

3. The grasp-activated power switch for a hand-held power tool of claim 2, wherein a distal end of the inner channel is configured for threaded engagement with a distal end of the tool body between the maximum and the minimum positions.

4. The grasp-activated power switch for a hand-held power tool of claim 1, wherein the tool body further comprises an external battery pack electrically coupled to a tool motor.

5. The grasp-activated power switch for a hand-held power tool of claim 4, wherein the external battery pack is configured to power the tool motor on and off in response to pulse generated when the first pin and the second pin complete the electrical connection between the first conductor and the second conductor.

6. The grasp-activated power switch for a hand-held power tool of claim 1, wherein the outer shell has a generally cylindrical form.

7. The grasp-activated power switch for a hand-held power tool of claim 6, wherein the outer shell defines a hollow longitudinal space concentrically aligned within the tool body.

8. The grasp-activated power switch for a hand-held power tool of claim 7, wherein the tool body further comprises a moving shaft operatively connected thereto and wherein the hollow longitudinal space is configured to allow passage therethrough of the moving shaft connected to the tool body.

9. The grasp-activated power switch for a hand-held power tool of claim 1, wherein the outer shell further comprises internal threads at a distal end of the outer shell, the internal threads are configured for threaded engagement with a distal cap.

10. The grasp-activated power switch for a hand-held power tool of claim 1, wherein the tool motor is mechanically coupled to a needle plunger of a tattoo machine.

11. The grasp-activated power switch for a hand-held power tool of claim 10, wherein the needle plunger attaches to a tattoo needle that extends through a distal end of the outer shell, the tattoo needle having a depth of penetration based on the positioning of the outer shell about the tool body.

12. A grasp-activated power switch for a tattoo machine, comprising:
    a tool body having a distal working end, a power attachment end, a motor electrically coupled to the power attachment end and mechanically coupled to a needle plunger extending through the distal working end, a first and second conductor and an internal battery pack;
    wherein the motor is electrically coupled to one of the first conductor or the second conductor and to the internal battery pack, and wherein the internal battery pack is electrically coupled to the other of the first conductor or the second conductor;
    an outer shell having an inner conductive layer electrically coupled to a first pin and a second pin that extend toward the first and second conductors;
    the outer shell configured for attachment to the tool body, wherein the outer shell is electrically separated from the tool body;
    whereby a manual grasping force applied to the outer shell causes the first pin and the second pin to complete an electrical connection between the first conductor and the second conductor thereby energizing the motor.

13. The grasp-activated power switch for a tattoo machine of claim 12, wherein the power attachment end is configured to attach an external battery pack.

14. The grasp-activated power switch for a tattoo machine of claim 12, wherein the power attachment end is configured to attach an external power cord wired to a power source.

15. The grasp-activated power switch for a tattoo machine of claim 12, wherein the inner channel is configured to attach to the distal working end of the tool body via threaded engagement.

16. The grasp-activated power switch for a tattoo machine of claim 15, wherein the outer shell is attachable to the distal working end between a maximum operating position and a minimum operating position, wherein the first pin and second pin are configured to contact the first conductor and second conductor when the outer shell is attached to the distal working end between the maximum and the minimum operating positions.

17. The grasp-activated power switch for a tattoo machine of claim 12, wherein outer shell generally has a cylindrical form and defines a hollow longitudinal space concentrically aligned with the tool body and the distal working end.

18. A grasp-activated power switch for a tattoo machine, comprising:
    an outer shell having an inner conductive layer electrically separated from the tattoo machine;
    a first pin and a second pin, each of the first pin and the second pin electrically coupled to the inner conductive;
    the outer shell configured for attachment to the tattoo machine, the tattoo machine having a first conductor, a second conductor, a battery, and a motor;
    the motor is electrically coupled to one of the first conductor or the second conductor and to the battery;
    the battery is electrically coupled to the other of the first conductor or the second conductor;
    whereby a manual grasping force applied to the outer shell causes the first pin and the second pin of the inner conductive layer to complete an electrical connection between the first conductor and the second conductor thereby energizing the motor.

19. The grasp-activated power switch for a tattoo machine of claim 18, wherein the tattoo machine has a distal working end that defines a maximum and minimum operating position, wherein the power switch is operational to complete the electrical connection between the first conductor and second conductor when an inner channel is attached to the distal working end between the maximum and minimum positions.

* * * * *